(12) United States Patent
Ardehali

(10) Patent No.: US 10,034,985 B2
(45) Date of Patent: Jul. 31, 2018

(54) INJECTION APPARATUS WITH NEEDLE HOUSING FOR DESENSITISING SKIN

(76) Inventor: Massoud Hosseini Ardehali, Chelsfield (GB)

( * ) Notice: Subject to any disclaimer, the term of this patent is extended or adjusted under 35 U.S.C. 154(b) by 0 days.

(21) Appl. No.: 14/110,908

(22) PCT Filed: May 24, 2012

(86) PCT No.: PCT/GB2012/051163
§ 371 (c)(1),
(2), (4) Date: Oct. 9, 2013

(87) PCT Pub. No.: WO2012/168691
PCT Pub. Date: Dec. 13, 2012

(65) Prior Publication Data
US 2014/0031747 A1   Jan. 30, 2014

(30) Foreign Application Priority Data
Jun. 9, 2011   (GB) .................................. 1109620.3

(51) Int. Cl.
*A61M 5/00* (2006.01)
*A61M 5/42* (2006.01)
(Continued)

(52) U.S. Cl.
CPC .......... *A61M 5/422* (2013.01); *A61M 5/2425* (2013.01); *A61M 5/326* (2013.01); *A61M 5/3293* (2013.01); *A61M 2005/341* (2013.01)

(58) Field of Classification Search
CPC ............ A61M 5/422; A61M 2025/009; A61M 2005/341; A61M 25/0631; A61M 5/2425;
(Continued)

(56) References Cited

U.S. PATENT DOCUMENTS 5,188,617 A * 2/1993 Linder .......................... 604/232
5,242,418 A   9/1993 Weinstein
(Continued)

FOREIGN PATENT DOCUMENTS

| WO | WO 01/93931 | 12/2001 |
|---|---|---|
| WO | WO 01/93931 A1 | 12/2001 |
| WO | WO 02/20074 A1 | 3/2002 |

*Primary Examiner* — Kevin C Sirmons
*Assistant Examiner* — Leah Swanson
(74) *Attorney, Agent, or Firm* — Adam Bell; Matthew Kaser

(57) ABSTRACT

A needle housing having a distal end which is removably connectable to a source of injectable fluid and a proximal end for contacting a patient, as well as to an injection apparatus comprising the needle housing. The needle housing comprises (a) a hollow needle through which the injectable fluid is deliverable to the patient, the needle having a proximal end for insertion into body tissue of the patient, and (b) a chamber having an open proximal end, the chamber surrounding at least part of the needle and extending proximally beyond the proximal end of the needle to the open proximal end. The open proximal end of the chamber is deformable and is moveable relative to the needle from a position in which the chamber extends proximally beyond the proximal end of the needle to a position in which the proximal end of the needle extends proximally through the open proximal end of the chamber.

16 Claims, 8 Drawing Sheets

(51) Int. Cl.
*A61M 5/24* (2006.01)
*A61M 5/32* (2006.01)
*A61M 5/34* (2006.01)

(58) Field of Classification Search
CPC ............... A61M 5/326; A61M 5/3293; A61M 2005/3254; A61M 2005/3258; A61M 2005/3267; A61M 2005/3268
USPC ................................ 604/112, 192, 198, 263
See application file for complete search history.

(56) References Cited

U.S. PATENT DOCUMENTS

| | | | |
|---|---|---|---|
| 5,290,254 A * | 3/1994 | Vaillancourt | 604/192 |
| 5,505,694 A | 4/1996 | Hubbard | |
| 6,537,242 B1 * | 3/2003 | Palmer | 604/22 |
| 6,743,211 B1 | 6/2004 | Prausnitz | |
| 6,752,817 B2 * | 6/2004 | Flora et al. | 606/181 |
| 7,037,294 B2 * | 5/2006 | Luther et al. | 604/192 |
| 7,147,624 B2 | 12/2006 | Hirsiger | |
| 2003/0078546 A1 | 4/2003 | Jensen | |
| 2005/0137531 A1 * | 6/2005 | Prausnitz et al. | 604/173 |
| 2009/0005743 A1 * | 1/2009 | Vaillancourt et al. | 604/263 |
| 2009/0181411 A1 * | 7/2009 | Battrell | B01F 11/0071 435/7.92 |
| 2012/0130340 A1 * | 5/2012 | Knutson | 604/506 |

* cited by examiner

INJECTION APPARATUS WITH NEEDLE HOUSING FOR DESENSITISING SKIN

The present application is a U.S. national phase application under 35 U.S.C. 371 of PCT/GB2012/051163 and claims priority from GB application 1109620.3 filed on 9 Jun. 2007 which is hereby incorporated by reference for all purposes.

This invention relates to an injection apparatus, and in particular to a needle housing, for use when injecting a patient in order to reduce the level of pain or discomfort felt by the patient. The invention also relates to a method for using the needle housing and injection apparatus.

It is well known to inject fluids into patients for a variety of reasons. Such injections are commonly carried out using a hollow needle with a bevelled tip, typically a hypodermic needle, which is connected to a syringe containing the fluid to be injected. The fluid is commonly contained within a cartridge which fits into the syringe. The syringe normally comprises a cylindrical barrel within which the cartridge is fitted, and a plunger which is slidably fitted within the barrel.

The injection usually involves piercing a patient's body tissue, for example their skin, with the needle. The plunger is then pushed towards the needle in order to deliver the fluid from the syringe, through the hollow needle, to the patient.

Often, the fluid that is injected into patients is a liquid comprising an anaesthetic, particularly a local anaesthetic. Local anaesthetic injections are commonly given in order to numb an area of a patient's body prior to surgery. A field of application for such injections is dentistry, in particular dental surgery. For example, a dental surgeon may inject a local anaesthetic into a part of a patient's mouth, for example a gum or other part of the mucosa, prior to carrying out dental surgery or performing a dental filling.

A problem with such anaesthetic injections is that the act of injecting the anaesthetic prior to surgery can itself cause pain and discomfort to a patient. The pain and discomfort can be caused by the piercing of the patient's body tissue by the needle and/or by the motion of the fluid as it is delivered through the needle to the patient.

Current methods of attempting to reduce the problem of the pain caused by injections include applying a topical anaesthetic solution or cream (eg Eutectic Mixture of Local Anaesthetics or EMLA) to the area on a patient's body where the injection is to be performed. The solution would normally be applied to the patient's body, for example the mucosa, using a cotton-tipped applicator stick. However, such topical anaesthetic creams and solutions generally need to be applied at least half an hour before an injection is performed in order for sufficient numbness to develop in the relevant area of the patient's body. This delay can be unsatisfactory. Also, the depth of numbness provided by such solutions is often inadequate unless they are left in contact for a considerable time (eg 30 minutes to 1 hour).

A problem with using such topical anaesthetic solutions when carrying out dental procedures in a patient's mouth is that the patient's saliva tends to wash the solution away. In addition, patients often complain that the taste of the topical anaesthetic solution is unpleasant.

A further known method for reducing the problem of the pain caused by injections is the application of an ethyl chloride spray to the area on a patient's body where the injection is to be performed. The anaesthetic effect of such sprays is caused by the cooling effect that they have on the area of the patient's body where they are sprayed. However, ethyl chloride spray has a number of problems. For example, the numbness caused by such sprays only lasts for a relatively short period of time, for example around 10-20 seconds. In addition, it can be difficult to focus the spray on a particular area on a patient's body. Also, if the spray is applied to an area in a patient's mouth, it is common for the patient to inhale some of the spray.

An alternative known means for trying to reduce the pain and discomfort caused by injections is to apply vibration to the area on a patient's body where the injection is to be performed. This is thought to send touch impulses which reduce a patient's perception of pain (according to the gate theory of pain).

A known method for attempting to reduce the problem of the pain and discomfort caused by piercing of the patient's body tissue by the needle and the motion of the fluid as it is injected through the needle into the patient involves controlling the rate at which the fluid is delivered to the patient using a microprocessor. This is generally carried out by controlling the rate at which the plunger of a syringe connected to the needle advances along the barrel. In addition, a finer needle is often used. It is believed that slower delivery of the fluid causes less discomfort to the patient. However, such methods generally require an expensive microprocessor, expensive disposable tips, and may take a few minutes to perform the injection. A further method is to shoot a jet of local anaesthetic onto the mucosa. The sound produced by this method can be startling for some patients.

A way of ameliorating these problems has been sought.

In accordance with this invention there is provided a needle housing having a distal end which is removably connectable to a source of injectable fluid and a proximal end for contacting a patient, the needle housing comprising:
  (a) a hollow needle through which the injectable fluid is deliverable to the patient, the needle having a proximal end for insertion into body tissue of the patient, and
  (b) a chamber having an open proximal end, the chamber surrounding at least part of the needle and extending proximally beyond the proximal end of the needle to the open proximal end, wherein the open proximal end of the chamber is deformable and is moveable relative to the needle from a position in which the chamber extends proximally beyond the proximal end of the needle to a position in which the proximal end of the needle extends proximally through the open proximal end of the chamber.

The needle housing as described above means that, in use, the open proximal end of the chamber contacts the patient's body tissue, but initially the needle does not. The contact of the deformable open proximal end of the chamber with the patient's body tissue preferably at least partially seals the open end of the chamber. Preferably a fluid-tight seal is formed, ie such that there is minimal or no leakage of injectable fluid from the proximal end of the chamber. By providing an open proximal end which is deformable, the needle housing of this invention allows the user to create a better seal with the patient's skin or mucosa. This is particularly important when carrying out injections on the mucosa, since area being injected is often curved and is normally more uneven than a patient's skin.

The injectable fluid can then be delivered through the hollow needle and out from its proximal end such that the chamber fills with the injectable fluid. The chamber may be adjusted at this point in order to allow any air in the chamber to escape, for example by breaking the at least partial seal between the skin/mucosa and the open proximal end. The at least partial seal can then be re-formed. This release of air from the chamber can make it easier for the chamber to be filled with the injectable fluid. The fluid in the chamber causes the part of the patient's body tissue which preferably at least partially seals (more preferably which forms a fluid-tight seal) the open end of the chamber to absorb the injectable fluid. The rate and/or level of absorption can be increased by applying pressure to the fluid in the chamber. One way of doing this, if the source of injectable fluid is a syringe, is to continue to depress the plunger of the still partially filled (either with air or injectable fluid) syringe after the chamber has filled with fluid. An alternative, or additional, way of increasing the pressure of the fluid in the chamber requires a collapsible and/or deformable chamber, is by applying external pressure (eg finger pressure) to the chamber so that it at least partially collapses and/or deforms. Using either method, the pressure can assist in the fluid in the chamber being "pushed" across the patient's intact body tissue, for example their mucous membrane or skin.

Once a sufficient amount of injectable fluid has been absorbed by the part of the patient's body tissue which seals the open end of the chamber, ie such that sufficient numbness has developed, the proximal end of the needle is moved relative to the open proximal end of the chamber such that the needle extends proximally through the open proximal end of the chamber and allows the user to pierce the patient's skin with the needle and inject the required amount of injectable fluid. This can be achieved by providing a chamber which is moveable or slidable relative to the needle. Preferably, the chamber is collapsible and/or deformable. This means that the needle can be moved relative to the open proximal end of the chamber by applying force to the chamber such that it collapses and/or deforms. An advantage of injecting anaesthetic in this way is that it can mean that less anaesthetic needs to be injected into the patient, thereby reducing the risk of toxicity with anaesthetic solutions. This invention allows the patient's body tissue to be made numb to a variety of depths by the absorption method described above, such that the subsequent perforation of the tissue by the needle can be relatively painless. Further gentle injection through the needle can then be used to anaesthetise a larger area and/or greater depth.

When the injectable fluid is a local anaesthetic, this procedure can significantly reduce the pain and discomfort felt by a patient when receiving a local anaesthetic injection. Since the needle housing is removably connectable to the source of injectable fluid, a first injectable fluid, for example a local anaesthetic, can initially be delivered to make the area numb. With the needle still in the patient's skin, or deeper in their body tissue, the first source of injectable fluid can be disconnected from the needle housing and a second source of injectable fluid, for example a drug such as an antibiotic or a vaccine, can be removably connected to the needle housing. This can then be injected into the patient with less or no pain.

A further advantage of the chamber is that it helps to protect the user from accidentally piercing their own body tissue either before or after an injection is performed. This is because the chamber extends proximally beyond the proximal end of the needle.

In addition, the use of the chamber means that the area of numbness, for example in a patient's mouth during dental surgery, is reduced compared to that formed when an anaesthetic injection alone is used. The chamber also means that the needle is less visible, making the injection apparatus less visually threatening for the patient. The invention also allows a smaller amount of local anaesthetic to be used, reducing the occurrence and severity of any side-effects caused by the local anaesthetic.

By use of a suitably strong needle, the needle housing of the invention can be used to perforate the periosteum or even a patient's bone for an intraosseous injection, occasionally reducing the need for nerve block injections. The present invention can also be used in many other situations, for example during the insertion of intravenous cannulae prior to an operation, or in spinal injections or taps.

The term "proximal" is used in relation to this invention to refer to the parts of the needle housing and injection apparatus which, in normal use, are closest to the area on a patient's body tissue where the injection is to take place. The term "distal" is used in relation to this invention to refer to the parts of the needle housing and injection apparatus which, in normal use, are furthest from the area on a patient's body tissue where the injection is to take place.

In some embodiments, the chamber and/or the open proximal end comprises a deformable plastic, preferably silicone. If the chamber is collapsible and/or deformable, this means that when force is applied to the chamber, it at least partially collapses and/or deforms which allows the user to increase the pressure of the injectable fluid within the chamber. It is preferred that the chamber does not significantly expand when pressure is applied to an injectable fluid in the chamber during normal use. The collapsing/deformation of the chamber also makes it easier for the user to pierce the patient's body tissue with the needle. In some embodiments, the chamber is collapsible and/or deformable to an extent that, in use, allows the needle to pierce the body tissue of a patient. In some embodiments, the chamber is moveable or slidable in a distal direction such that the open proximal end of the chamber is moveable relative to the needle from a position in which the chamber extends proximally beyond the proximal end of the needle to a position in which the proximal end of the needle extends proximally through the open proximal end of the chamber. Preferably, the moveable or slidable chamber is sealably connected to the source of injectable fluid during its movement. This sealable connection could be achieved, for example, by using washers or rings.

In some embodiments, open proximal end and/or the chamber is resiliently sealable against the body tissue of a patient. The term "sealable" is used to mean a seal to the extent necessary to allow the chamber to at least partially fill, preferably substantially completely fill, more preferably completely fill, with the injectable fluid. In some embodiments, the open proximal end of the chamber in use is substantially sealed by the body tissue of a patient. In some embodiments, the open proximal end comprises a lip which is deformable and/or resiliently sealable against the body tissue of the patient. This assists in enabling a leak-proof contact (ie a good seal) to be made with the skin/mucosa which is to be injected.

In some embodiments, the open proximal end of the chamber has an area of 3.5 $cm^2$ or less. Preferably the area is 2 $cm^2$ or less, more preferably 1 $cm^2$ or less, even more preferably 0.5 $cm^2$ or less. In some applications, smaller areas can be useful in creating a greater pressure of fluid within the chamber so that more of the injectable fluid is absorbed through a patient's skin or mucosa.

In some embodiments, the needle housing comprises a gas permeable section which connects the chamber to the exterior of the device, but which is not permeable to the injectable fluid, preferably an injectable liquid. This can be useful in helping air to escape from the chamber when filling the chamber with the injectable fluid. In some embodiments, the needle housing comprises a closable opening which connects the chamber to the exterior of the device, for example a vent, to allow air to escape when filling the chamber with injectable fluid. In this way, the release of air from the chamber can be controlled, making it easier for the chamber to be filled with injectable fluid. In some embodiments, the closable opening comprises a valve. In some embodiments, the closable opening comprises an aperture and either a stopper or flap (eg a hinged door) which closes the aperture. In some embodiments, the gas permeable section and/or the closable opening connect the chamber to a depression on an exterior of a substantially rigid connector (described below). This allows the user to control the flow of air through the gas permeable section and/or the closable opening by covering them with their finger or thumb. Once air has been allowed to escape, the gas permeable section can be sealed in order to enable the increase of pressure of the fluid in the chamber as described above.

In some embodiments, the proximal end of the needle is bevelled. The needle is normally shaped in this way in order to make it easier for the user to pierce the patient's body tissue. Preferably, the needle is a hypodermic needle. In some embodiments, the proximal end of the needle is sharp. In some embodiments, the proximal end of the needle is non-bevelled. Such needles can be useful for intra-osseous injections, because the needle is less likely to bend.

In some embodiments, the needle housing comprises a substantially rigid connector at its distal end. Preferably, the needle housing is sealably connectable to the source of injectable fluid. In some embodiments, the needle housing is removably connectable to the source of injectable fluid by an interference fitting, a friction fitting, a Luer lock, or a screw thread. In this way, the needle housing can easily be attached and/or detached from the source of injectable fluid, for example if the needle housing is to be connected to a different (eg second) source of injectable fluid, or if the needle housing is to be disposed of (eg in a sharp bin) after use. In some embodiments, the substantially rigid connector comprises a Luer lock connector and/or a screw thread. Preferably, the needle housing is disposable.

In some embodiments, the substantially rigid connector is provided with a depression on its external surface. The user can press the depression with their finger in order to assist in stabilising the chamber against the skin or mucosa. Pressing the depression also enables the collapsing/deformation of the chamber, increasing the pressure of the injectable fluid in the chamber as well as helping to move the needle towards the patient such that it pierces the patient's body tissue.

In some embodiments, the needle has a distal end which protrudes distally at the distal end of the housing. In some embodiments, the distal end of the needle is bevelled. This distal bevel can be useful when the source of injectable fluid, for example a syringe, is the type that is shaped to accept cartridges of injectable fluid. Such cartridges are normally provided with a seal comprising a pierceable membrane, normally made from a latex-free material or rubber, at their proximal end. The bevel at the distal end of the needle makes it easier to pierce the membrane in order to provide access to the injectable fluid.

In some embodiments, the needle is bent. In some embodiments, the needle is bent through an angle of at least 30 degrees, preferably less than 60 degrees. In some embodiments, the needle is bent through an angle of about 45 degrees. Providing a needle with a bend in it is particularly useful in dental surgery, where the bend can assist the user when trying to reach parts of the mouth that are difficult to access with a conventional straight needle. In some embodiments, the needle is straight. The use of a straight needle is preferred when performing an injection on an area of a patient which is relatively easy to access.

In some embodiments, the chamber is transparent and/or translucent. This can be useful in allowing the user to see how much fluid is in the chamber, as well as allowing them to visually determine the position of the needle relative to the patient's body tissue.

In some embodiments, the open proximal end of the chamber comprises a lip which curves away from the needle. In some embodiments, the lip is compressible and/or deformable. In some embodiments, the lip curves outwardly in a direction which is substantially perpendicular to the plane of the open proximal end. This lip can assist in providing a seal when the proximal end of the chamber is placed against the body tissue of a patient, for example against slightly curved mucosa or skin. An upper part of the lip can be lifted away from the body tissue of the patient to allow air to escape from the chamber when it is being filled with injectable fluid during use. The word "upper" is used in this context to refer to up with respect to gravity, since the injectable fluid will fill the chamber under gravity from a lower to an upper section. In some embodiments, the chamber is bell-shaped. The phrase "bell-shaped" is used to describe a chamber have a domed distal end and a proximally extending waist which widens to a lip at its open end.

In some embodiments, the proximal end of the needle housing additionally comprises an end cap which is removably attachable to the open proximal end of the chamber. The removable end cap may be provided in order to give the user additional protection against accidentally piercing their own body tissue either before or after an injection is performed. In addition, the needle housing would normally be supplied in a sterilised condition and the removable end cap can help to maintain the sterilised condition of the chamber, and therefore the needle. After use, both the needle housing and the end cap can be disposed of in a sharp box.

In some embodiments, the source of injectable fluid comprises a syringe. In some embodiments, the syringe is shaped to accept cartridges of injectable fluid, preferably a liquid. A suitable syringe would be a breech-loading syringe, or a pressure syringe or intraligamental syringe. The syringe can be a single-use disposable syringe, or a multiple-use syringe. Preferably, the source of injectable fluid is disposable.

In some embodiments, the source of injectable fluid comprises a collapsible compartment containing injectable fluid. In some embodiments, the collapsible compartment comprises a membrane at a proximal end, preferably made of a latex-free material or rubber, which is pierceable by the distal end of the needle. In some embodiments, the collapsible compartment has a concertina-shaped wall. Preferably, the collapsible compartment comprises a deformable plastic, preferably silicone.

In some embodiments, the injectable fluid comprises an anaesthetic, preferably a local anaesthetic. Particularly preferred local anaesthetics include lidocaine, prilocaine, articaine, and mixtures thereof. In some embodiments, the injectable fluid comprises a vaccine. In some embodiments, the injectable fluid is a liquid.

According to the invention there is also provided an injection apparatus comprising the needle housing as described above.

In accordance with the invention there is also provided a method for injecting fluid into a patient, the method comprising the steps of:

(a) providing a chamber having a deformable open proximal end, (b) placing the deformable open proximal end against an area of a patient's body tissue such that the patient's body tissue at least partially seals the open end of the chamber, (c) at least partially filling the chamber with an injectable fluid such that the area of the patient's body tissue absorbs at least some of the fluid, and (d) injecting the area of the patient's body tissue which has absorbed the fluid.

In some embodiments, in step (b) the open proximal end and/or the chamber forms a resilient seal against the patient's body tissue. In some embodiments, in step (b) the patient's body tissue substantially seals the open end proximal of the chamber. This can help to increase the rate of absorption of anaesthetic in step (c). In some embodiments, the chamber is collapsible and/or deformable. In some embodiments, the method includes a step in between steps (c) and (d) of collapsing and/or deforming the chamber. In some embodiments, the injection in step (d) comprises piercing the patient's body tissue with a needle.

In some embodiments, in step (c) the chamber is substantially filled, preferably completely filled, with the injectable fluid. In some embodiments, in step (c) the fluid in the chamber is pressurised. This is done in order to increase the rate and/or level of absorption of the fluid by the patient's body tissue. In some embodiments, fluid in the chamber is pressurised by attempting to continue to supply fluid to the chamber after the chamber has been substantially filled. In some embodiments, the fluid in the chamber is pressurised by at least partially collapsing and/or deforming the chamber. In some embodiments the fluid is a liquid. In some embodiments, the liquid comprises an anaesthetic, preferably a local anaesthetic.

In some embodiments, in step (c) whilst the chamber is being at least partially filled with injectable fluid, the open proximal end of the chamber is only partially sealed against the area of the patient's body tissue such that air can escape from the chamber as it is filled. In some embodiments, the partial seal is formed such that the air can escape from an upper half of the open proximal end. The word "upper" is used in this context to refer to up with respect to gravity, since the injectable fluid will fill the chamber under gravity from a lower to an upper section. Alternatively, the chamber is provided with a gas permeable section or a closable opening, through which air can escape as the chamber is filled.

In some embodiments, the chamber is filled using a syringe. The syringe typically comprises a cylindrical barrel and a plunger. In some embodiments, the chamber is pressurised by continuing to press the plunger after the chamber has filled with fluid and/or by applying pressure to the chamber, for example by pressing a depression on a substantially rigid connector connected to a distal end of the chamber.

In some embodiments, the chamber is filled by collapsing a collapsible compartment containing injectable fluid. In some embodiments, the collapsible compartment has a concertina-shaped wall. In some embodiments, the chamber is pressurised by continuing to cause the collapsible compartment to collapse after the chamber has filled with fluid.

In some embodiments, the chamber is part of a needle housing as described above. In some embodiments, the injection is performed using the needle of the needle housing.

In some embodiments, the method includes an additional step (e) after step (d), of injecting the area of the patient's body tissue which has absorbed the fluid with a second, different, injectable fluid. Where the chamber is part of the needle housing as described above, method step (e) comprises disconnecting a first source of injectable fluid from the needle housing and removably connecting a second source of injectable fluid to the needle housing. In some embodiments, the injectable fluid of the first source comprises a local anaesthetic. In some embodiments, the injectable fluid of the second source comprises a drug, for example an antibiotic or a vaccine.

The needle housing and injection apparatus of the invention is intended initially to make the surface of the mucosa or skin insensitive by applying topical local anaesthetic under pressure. The proximal end of the needle of the injection apparatus is then used to penetrate the underlying numb area and inject, preferably painlessly, a further supply of standard local anaesthetic solution. This comfortably achieves the desired numbness of adjacent flesh and other nearby innervated structures, prior to starting the treatment.

The supply of the local anaesthetic could be from a standard dental syringe and dental cartridge or a local anaesthetic-containing collapsible compartment as described herein.

When used in the field of dentistry, the needle housing may be shaped such that it is screwable onto a dental syringe. The cartridge containing the local anaesthetic can then be loaded into the cavity of the syringe. Alternatively, a disposable syringe and cartridge can be attached to the needle housing. The proximal end of the chamber of the needle housing, preferably comprising a lip, is placed on the mucosa and the plunger of dental cartridge is advanced to propel the local anaesthetic through the needle and to expel air and to fill the chamber. Further increase in the pressure of the anaesthetic solution in the chamber pushes the fluid through the intact underlying mucosa and achieves surface numbness of variable depth. This compression of the anaesthetic solution increases the permeation, depth and speed of numbing of the underlying tissues. The extent of numbness would be proportional to the time used to keep the pressurised anaesthetic solution in contact with the mucosa. The injection apparatus is so shaped that it can be held comfortably in one location for a few minutes. When surface numbness is assumed, the top of the chamber is pushed. As the chamber is preferably compressible, this causes the proximal end of the, preferably centrally placed, needle to penetrate the insensitive area of the mucosa. At this time the local anaesthetic is slowly injected into the underlying tissues to achieve a larger area of numbness. This enables effective injection of the local anaesthetic, preferably painlessly.

Instead of a dental cartridge, an alternative source of anaesthetic can be used. This companion to the device can be a labelled collapsible compartment prefilled with an appropriate local anaesthetic solution. It is preferably concertina or barrel shaped and collapsible with the ability to propel its contents if collapsed, for example by pressing on its distal end. The proximal end is preferably cylindrical and threaded such that it can be screwed onto the distal end of the needle housing. When joined together (same as a standard dental needle and a dental syringe) the distal end of the needle penetrates the membrane of the anaesthetic container. On pressing the top of the container, the solution is ejected via the proximal end of needle into the chamber. The device is then used in a similar fashion described above. That is, after achieving topical anaesthesia; the proximal end of the needle is advanced through the mucosa or skin. A dose of the local anaesthetic can then be given by compressing the chamber and propelling its contents into the tissues below and obtaining local analgesia.

When injecting the skin, the source of local anaesthetic is usually from a glass phial or ampoule. When used with the present invention, the liquid is preferably aspirated into a plastic syringe and connected to the device. Once local analgesia is achieved, the procedure or operation can be carried out.

An additional use of the needle housing is to numb an area and then, using the same apparatus, inject a drug or other materials into the underlying insensitive tissues. Once numbness is assumed, the source of local anaesthetic, for example a syringe with the anaesthetic supply, can be removed. With the needle still in the tissues, a different source of injectable fluid, for example a plastic syringe already filled by the appropriate volume of drugs such as antibiotics or vaccines, is then preferably connected. Using the same apparatus, the medication or material can then be injected into the tissues, preferably painlessly.

This invention will be further described by reference to the following Figures which are not intended to limit the scope of the invention claimed, in which:

FIGS. 7A-D show various types of needle housing and sources of injectable fluid in accordance with the invention.

Figure 1:
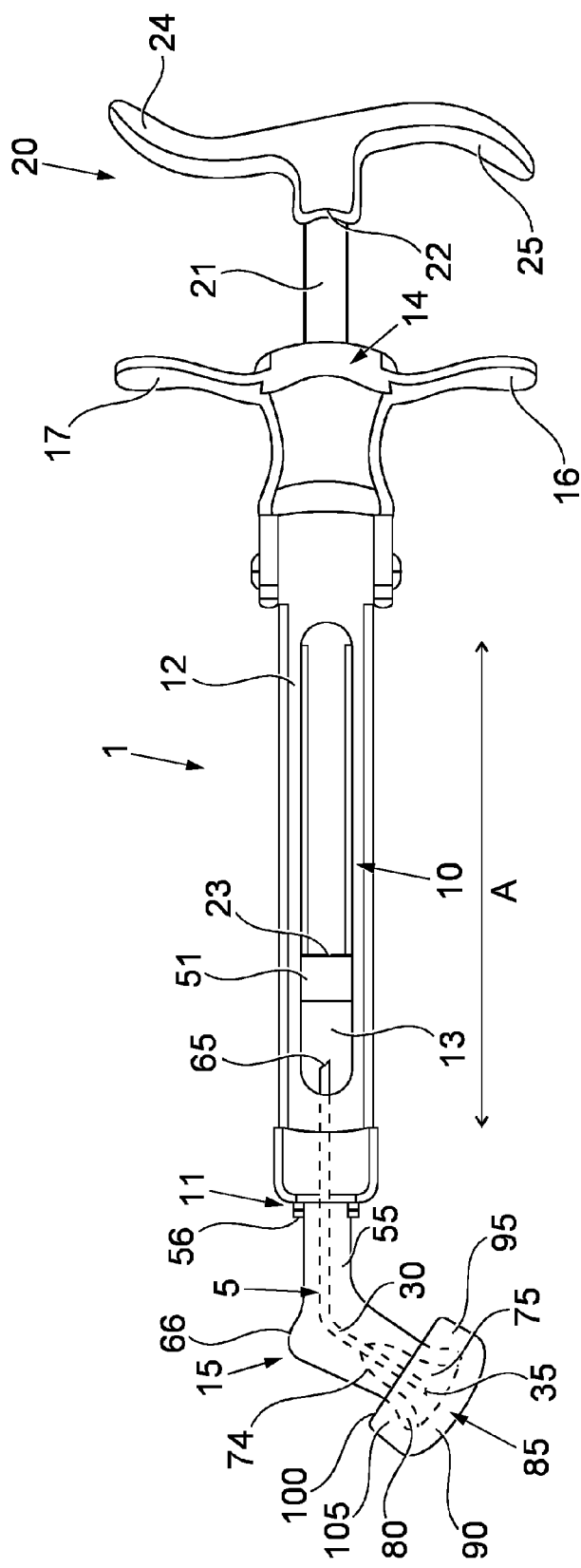
FIG. 1 shows a needle housing in accordance with one embodiment of the invention when part of an injection apparatus.
Figure 2:
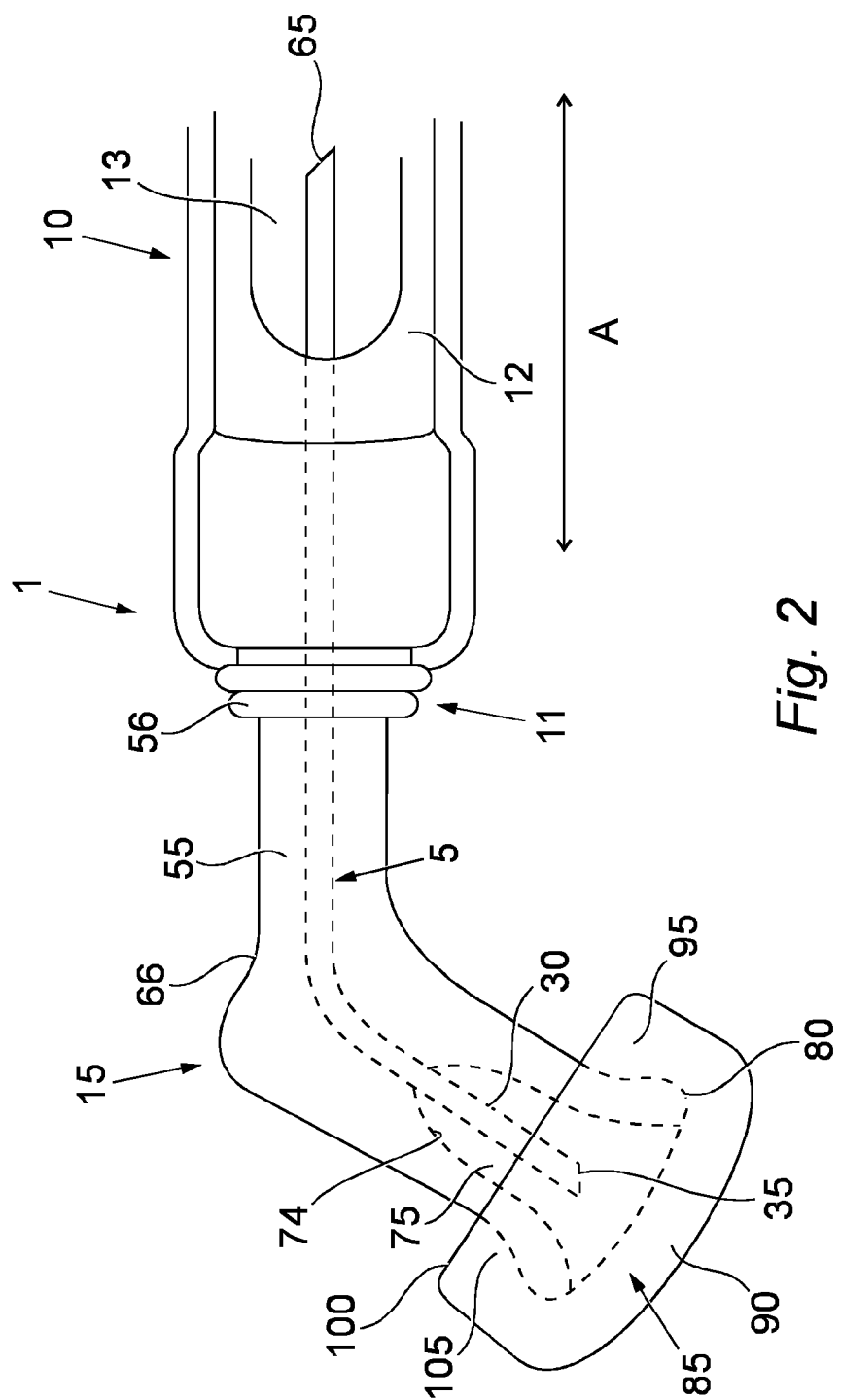
FIG. 2 shows an enlarged view of the proximal end of the injection apparatus of FIG. 1.
Figure 3:
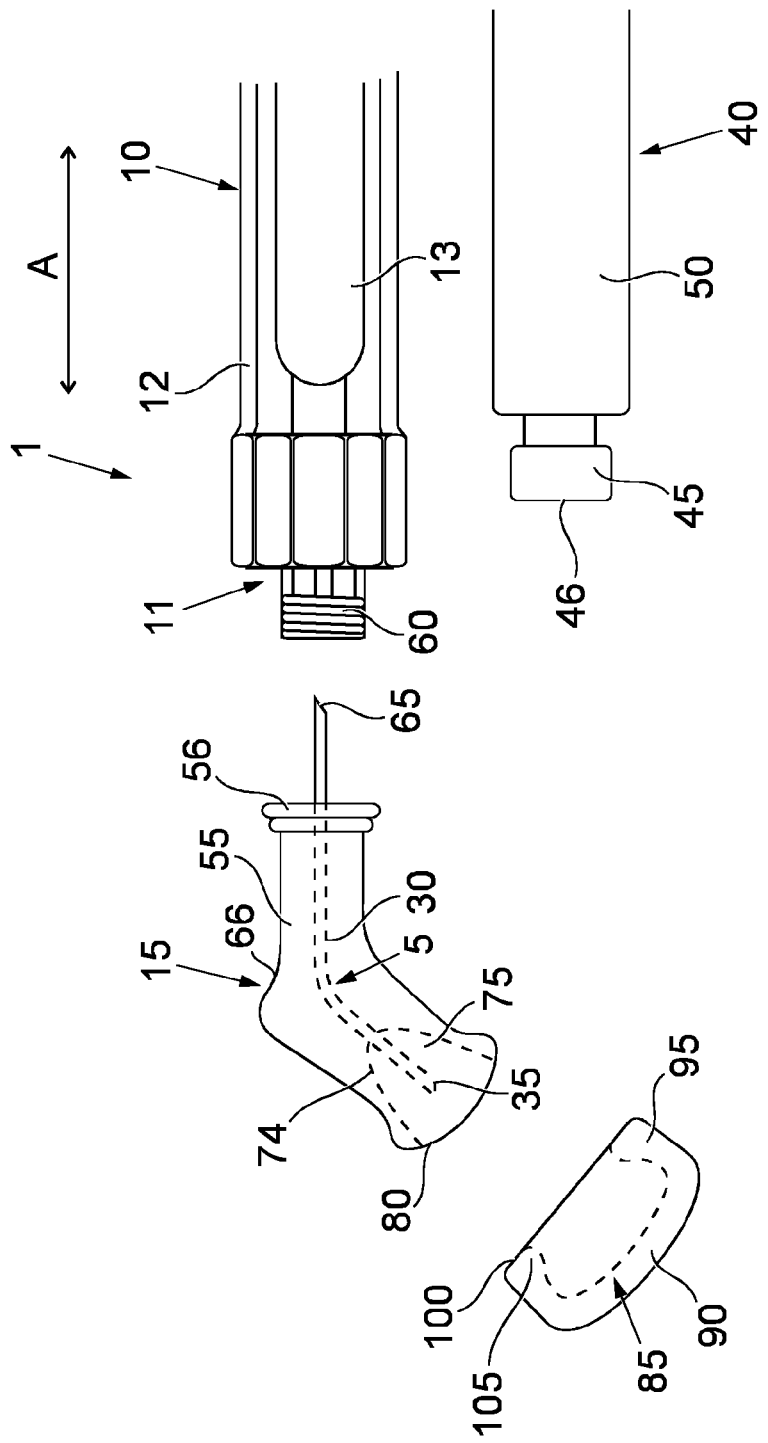
FIG. 3 shows an exploded view of the proximal end of the injection apparatus of FIG. 1 and a cartridge of injectable fluid.
Figure 4:
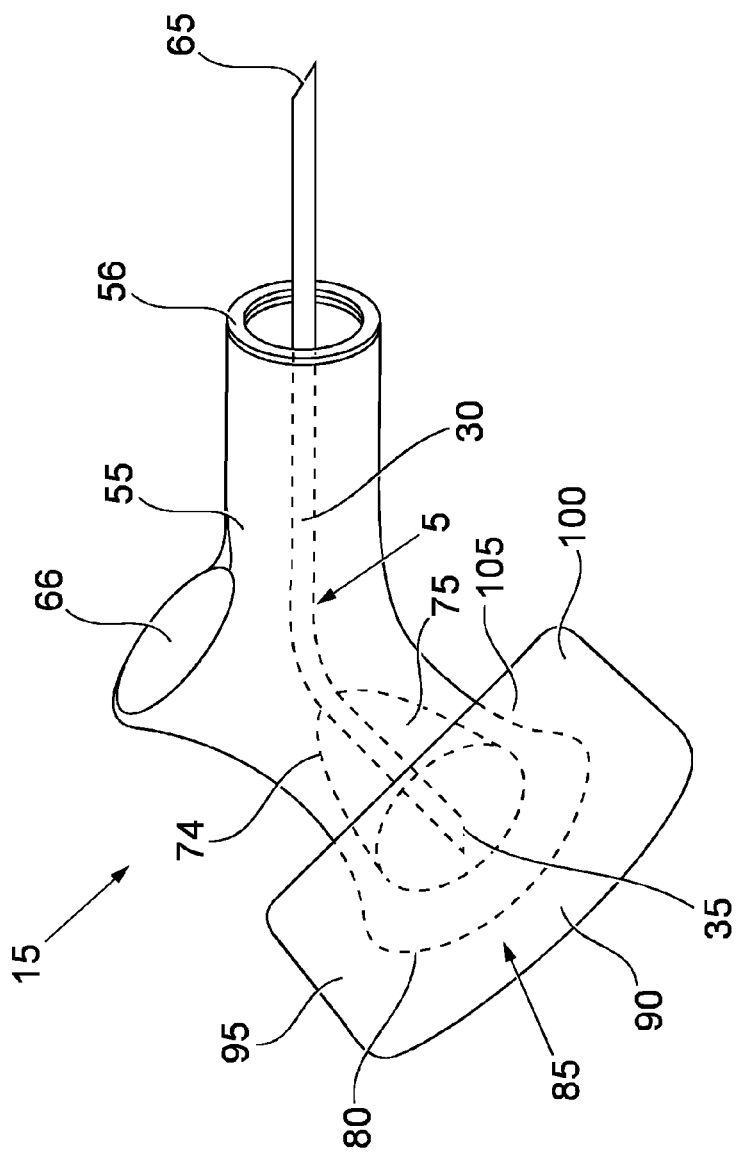
FIG. 4 shows an enlarged view of the needle housing of FIG. 1.

FIG. 1-4 depict a needle housing 15 in accordance with one embodiment of the invention. In FIGS. 1-3, the needle housing 15 is shown as part of an injection apparatus 1. The injection apparatus 1 comprises a breech-loading syringe 10 which is connected at its proximal end 11 to the needle housing 15. The needle housing comprises a deformable chamber 75 which surrounds and extends proximally beyond a needle 5. The injection apparatus 1 has a major axis A which is parallel to the syringe 10.

As shown in FIGS. 1-3, the syringe 10 comprises a cylindrical tube 12 and a plunger 20 (only shown in FIG. 1) which is slidably fitted within the tube 12. The cylindrical tube 12 is made mainly of metal (but alternatively could be made of a disposable plastic material), but with two slots 13 provided in opposite sides of the tube 12. The slots 13 are provided to assist the user in determining the position of the plunger 20 within the cylindrical tube 12.

As shown in FIG. 1, at its distal end 14 the syringe 10 is provided with two syringe finger grips 16,17. Syringe finger grips 16,17 are in the form of metal tabs which extend in opposite directions from syringe 10 and substantially perpendicularly to the major axis A of injection apparatus 1. Syringe finger grips 16,17 are provided to make it easier for the user to hold the injection apparatus 1.

As is known in the art, cylindrical tube 12 is shaped to accept cartridges of fluid (in particular a liquid) comprising a local anaesthetic. An example of such a cartridge 40 is shown in FIG. 3. The cartridge 40 comprises a metal cap 45 which is provided with a latex-free membrane (not shown) on a proximal surface 46 for piercing by the needle 5. The cartridge 40 also comprises a glass phial 50 which contains the fluid. Slidably fitted within glass phial 50 is bung 51 (shown in FIG. 1).

As also shown in FIG. 1, the plunger 20 comprises a solid cylindrical rod 21 which is slidably fitted within cylindrical tube 12. At the distal end 22 of rod 21 is provided a palm rest. The palm rest is in the form of metal tabs 24,25 which extend in opposite directions from rod 21 substantially perpendicularly to the major axis A of injection apparatus 1. The palm rest is designed to rest against the user's palm during use in order to make it easier for the user to hold the injection apparatus 1.

As is known in the art, the solid cylindrical rod 21 of plunger 20 is shaped such that in use its proximal end 23 abuts slidable bung 51.

The needle 5 of needle housing 15 is a hypodermic needle which, as is known in the art, comprises a hollow metal tube 30 with a proximal bevelled tip 35 (see FIGS. 1-4). The proximal bevelled tip 35 makes it easier for the user to pierce the body tissue of the patient who is to receive the injection.

The needle 5 is connected to, and passes through the centre of, solid rigid annular plastic collar 55 of needle housing 15. The collar 55 has an internal cylindrical cavity at its distal end 56 which is provided with a screw thread (not shown). The screw thread on the collar 55 is shaped to cooperate with external screw thread 60 (see FIG. 3) provided at the proximal end 11 of syringe 10. The collar 55 also has depression 66 which the user can press with their finger during use in order to deform the deformable chamber 75.

As shown in FIGS. 1-4, the needle 5 protrudes distally from collar 55 and is provided with a distal bevelled tip 65 which is substantially identical in shape to proximal bevelled tip 35. As shown in FIGS. 1 and 2, when the collar 55 is screwed onto external screw thread 60 of syringe 10, the needle extends distally within cylindrical tube 12 of syringe 10 such that when a cartridge 40 is fitted within the tube 12 the distal bevelled tip 65 pierces the latex-free membrane and contacts the fluid within the cartridge 40.

The needle 5 initially extends proximally through collar 55 within needle housing 15 in a direction coincident with major axis A of the injection apparatus 1. At approximately halfway between the proximal end 11 of syringe 10 and the proximal bevelled tip of needle 5, the needle 5 is bent in a direction approximately 45° to major axis A. The bend in needle 5 is not essential, but is particularly useful for applications in dental surgery where it can assist the user in accessing certain parts of a patient's mouth.

Extending proximally from collar 55 and surrounding needle 5 is deformable chamber 75 of needle housing 15. Deformable chamber 75 is normally made of a transparent deformable plastic such as silicone. Deformable chamber 75 is formed around the part of needle 5 which is bent in a direction approximately 45° to major axis A.

Deformable chamber 75 has a domed distal end 74 and it curves outwardly at its proximal end 80 to form lip such that chamber 75 is substantially bell-shaped. The proximal end 80 of deformable chamber 75 extends proximally beyond the proximal bevelled tip 35 of needle 5 such that, if proximal end 80 was rested on a flat surface (without applying pressure to deform the deformable sleeve 15), the proximal bevelled tip 35 of needle 5 would not contact the surface.

As shown in FIGS. 1-4, the proximal end 80 of deformable chamber 75 is provided with a removable end cap 85 (shown in section). The end cap is made of a deformable material such as a deformable plastic or latex-free material and comprises a circular base 90 and an annular wall 95. The annular wall 95 is provided at its edge 100 with an annular lip 105. The annular lip 105 is shaped to grip the outward curve of proximal end 80 of deformable chamber 75.

During use, the part of the patient's body tissue where the injection is to take placed is first cleaned with an antiseptic swab. A cartridge 40 of local anaesthetic-containing fluid is then placed in cylindrical tube 12 of syringe 10. Plunger 20 is then inserted into the cylindrical tube such that its proximal end 23 abuts slidable bung 51. Needle housing 15 is then connected to syringe 10 by screwing collar 55 onto external screw thread 60 at proximal end 11 of syringe 10 such that distal bevelled tip 65 of needle 5 pierces the latex-free membrane of cartridge 40.

The proximal end 80 of deformable chamber 75 of needle housing 15 is then placed in contact with the part of a patient's body tissue where the injection is to take place. In dental surgery, this is commonly a part of the patient's oral mucosa. In this way, the chamber 75 is substantially resiliently sealed by deformation at its proximal end 80 against the patient's body tissue. At this stage in the procedure, the proximal bevelled tip 35 of needle 5 is not in contact with the patient's body tissue.

The plunger 20 of syringe 10 is then slid in a proximal direction, which causes bung 51 to slide in a proximal direction, such that the anaesthetic-containing fluid flows into distal bevelled tip 65 of needle 5, along hollow metal tube 30 and out from proximal bevelled tip 35. As a result of chamber 75 being substantially sealed, the chamber 75 fills with the local anaesthetic-containing fluid. The chamber 75 may be adjusted slightly during filling in order to allow air to escape and be replaced in the chamber 75 by the local anaesthetic-containing fluid.

Once chamber 75 has been filled with the local anaesthetic-containing fluid, the user attempts to slide the plunger 20 further in a proximal direction such that the local anaesthetic-containing fluid in chamber 75 is pressurised. Alternatively or additionally, the fluid can be pressurised by at least partially collapsing and/or deforming the chamber 75. This helps the local anaesthetic-containing fluid to be absorbed through the part of the patient's body tissue that it is in contact with. The injection apparatus 1 is held in this position for a period of time, normally at least 30 seconds or more, such that the absorption of the local anaesthetic causes a sufficient degree of numbness to develop in the patient's body tissue. The part of the patient's body tissue which absorbs the anaesthetic-containing fluid can sometimes swell at this stage such that the distance between the patient's body tissue and the proximal bevelled tip 35 of needle 5 is reduced.

Force is then applied by the user to the injection apparatus 1 such that the deformable chamber 75 deforms and the proximal bevelled tip 35 of needle 5 pierces the patient's body tissue. Force may additionally be applied by the user by pressing the depression 66 of the collar 55. The anaesthetic-containing fluid remaining in cartridge 40 is then injected into the patient in the normal way known in the art.

By following the method described above, the pain and discomfort felt by the patient due to the piercing of the patient's body tissue by the needle and/or by the motion of the fluid as it is delivered through the needle to the patient is substantially reduced. This is achieved by causing the anaesthetic-containing fluid to initially be absorbed by the patient's body tissue prior to carrying out the injection.

Figure 5:
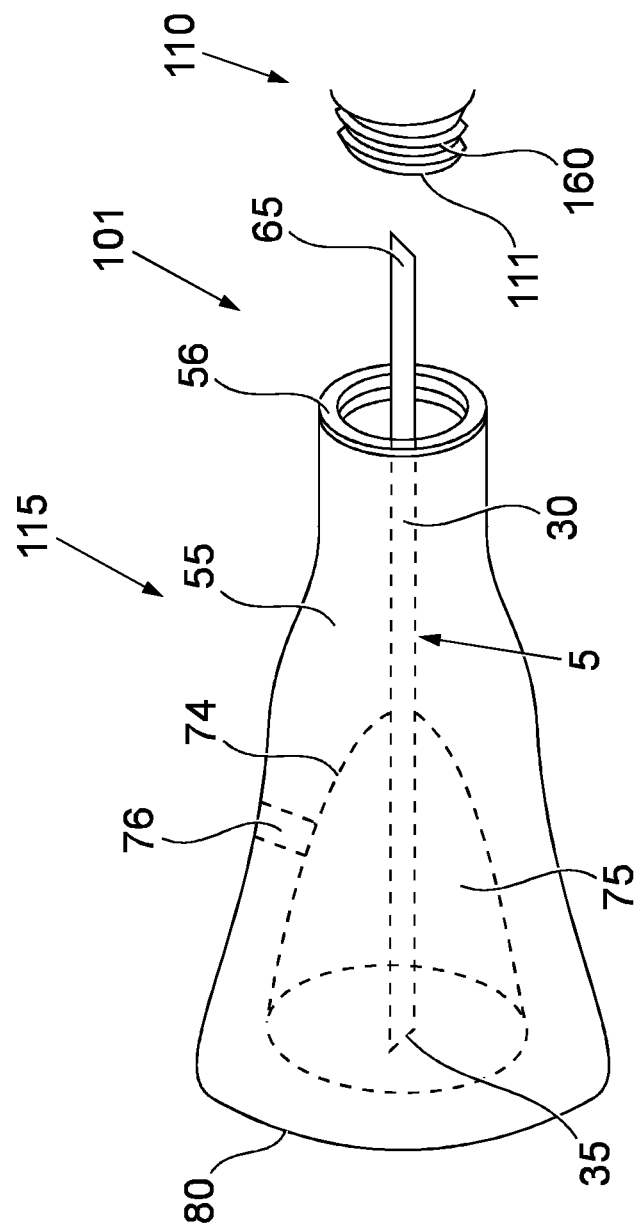
FIG. 5 shows an alternative embodiment of a needle housing in accordance with the invention in which the needle is straight.
Figure 6:
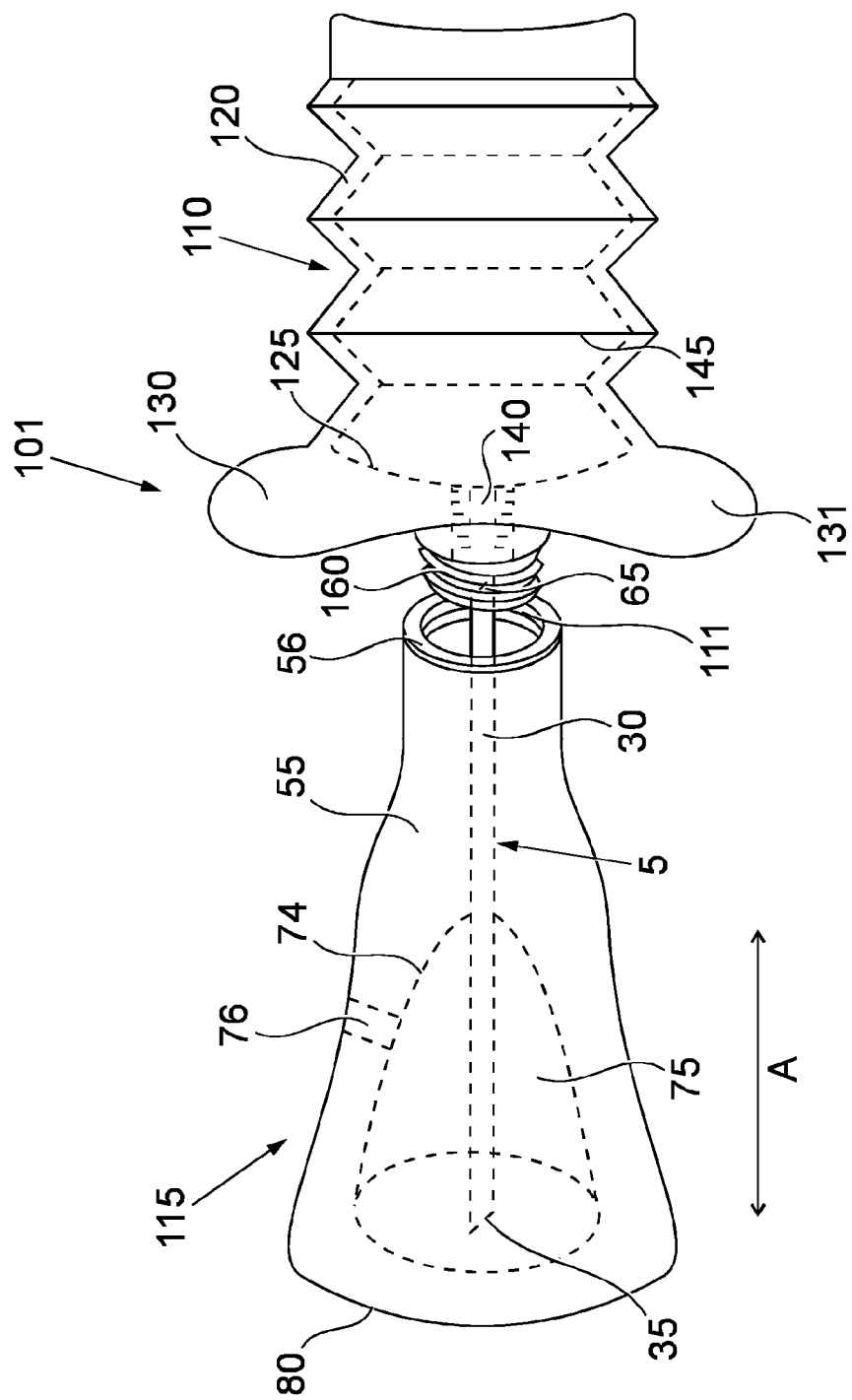
FIG. 6 shows the needle housing of FIG. 5 and an alternative source of injectable fluid in accordance with the invention.

FIGS. 5 and 6 depict an alternative needle housing 115 in accordance with the present invention, shown as part of injection apparatus 101. Features in common with the embodiment shown in FIGS. 1-4 are labelled with the same reference numerals.

The main difference between the needle housing 115 of FIGS. 5 and 6 and the needle housing 15 of FIGS. 1-4 is that the needle 5 of needle housing 115 is straight. Thus, needle 5 extends proximally through collar 55 and into deformable chamber 75 in a direction coincident with major axis A (shown in FIG. 6) of injection apparatus 1. In addition, collar 55 does not comprise depression 66 and the deformable chamber 75 comprises gas permeable section 76. Gas permeable section 76 could be replaced by a vent as described above.

The injection apparatus 101 of FIGS. 5 and 6 also differs from the injection apparatus 1 of FIGS. 1-4 in that it comprises a collapsible local anaesthetic container 110, instead of a syringe 10, which is connectable at its proximal end 111 to needle housing 115.

As shown in FIGS. 5 and 6, the container 110 is provided with an external screw thread 160 which is shaped to cooperate with a screw thread in internal cylindrical cavity at proximal end 56 of collar 55. FIG. 5 only shows the proximal end 111 of container 110, whereas FIG. 6 shows the whole container 110.

Collapsible compartment 145 (shown in sectional view in FIG. 6) extends distally from external screw thread 160. Compartment 145 contains a liquid comprising a local anaesthetic. Compartment 145 is generally cylindrical in shape and has a concertina wall 120. The wall is formed from a deformable plastic such as silicone.

At proximal end 125 of compartment 145 are provided two finger grips 130,131. Finger grips 130,131 are in the form of two rigid plastic tabs which extend in opposite directions from compartment 145 substantially perpendicularly to the major axis A of injection apparatus 101. Figure grips 130,131 are provided to make it easier for the user to hold injection apparatus 101.

Also at proximal end 125 of compartment 145, and between compartment 145 and external screw thread 160, is provided latex-free membrane 140.

In use, needle housing 115 is connected to container 110 by screwing collar 55 onto external screw thread 160 at proximal end 111 of container 110 such that distal bevelled tip 65 of needle 5 pierces latex-free membrane 140. In this way, distal bevelled tip 65 of needle 5 is brought into contact with the local anaesthetic-containing liquid within container 110.

The proximal end 80 of deformable chamber 75 of needle housing 115 is then placed in contact with the part of a patient's body tissue where the injection is to take place. In this way, the chamber 75 is substantially resiliently sealed by deformation at its proximal end 80 against the patient's body tissue. At this stage in the procedure, the proximal bevelled tip 35 of needle 5 is not in contact with the patient's body tissue.

Pressure is then applied to compartment 145 of container 110 such that the concertina wall 120 begins to collapse. This causes the anaesthetic-containing liquid to flow into distal bevelled tip 65 of needle 5, along hollow metal tube 30 and out from proximal bevelled tip 35. As a result of chamber 75 being substantially sealed, the chamber 75 fills with the local anaesthetic-containing liquid. Any air in chamber 75 can escape via gas permeable section 76.

However, since gas permeable section 76 is not permeable to the local anaesthetic-containing liquid, this liquid is retained in the chamber. Gas permeable section 76 could be replaced with a vent.

Once chamber 75 has been filled with the local anaesthetic-containing liquid, the user applies further pressure to the compartment 145 of container 110. This causes the concertina wall 120 to collapse further such that the local anaesthetic-containing fluid in chamber 75 is pressurised. This causes the local anaesthetic-containing fluid to be absorbed through the part of the patient's body tissue that it is in contact with. The injection apparatus 101 is held in this position for a period of time, normally at least 30 seconds or more, such that the absorption of the local anaesthetic causes a sufficient degree of numbness to develop in the patient's body tissue. The part of the patient's body tissue which absorbs the anaesthetic-containing fluid can sometimes swell at this stage such that the distance between the patient's body tissue and the proximal bevelled tip 35 of needle 5 is reduced.

Force is then applied by the user to the injection apparatus 101 such that the deformable chamber 75 deforms and the proximal bevelled tip 35 of needle 5 pierces the patient's body tissue. The anaesthetic-containing liquid remaining in compartment 145 of container 110 is then injected into the patient by applying additional pressure such that concertina wall 120 to collapses further. Once the area of the patient's body tissue has been anaesthetised, the container 110 can optionally be disconnected and an alternative container (not shown) can be connected to needle housing 115. The alternative container may contain other medications, such as antibiotics, which can then be injected into the patient substantially painlessly.

Figure 7:
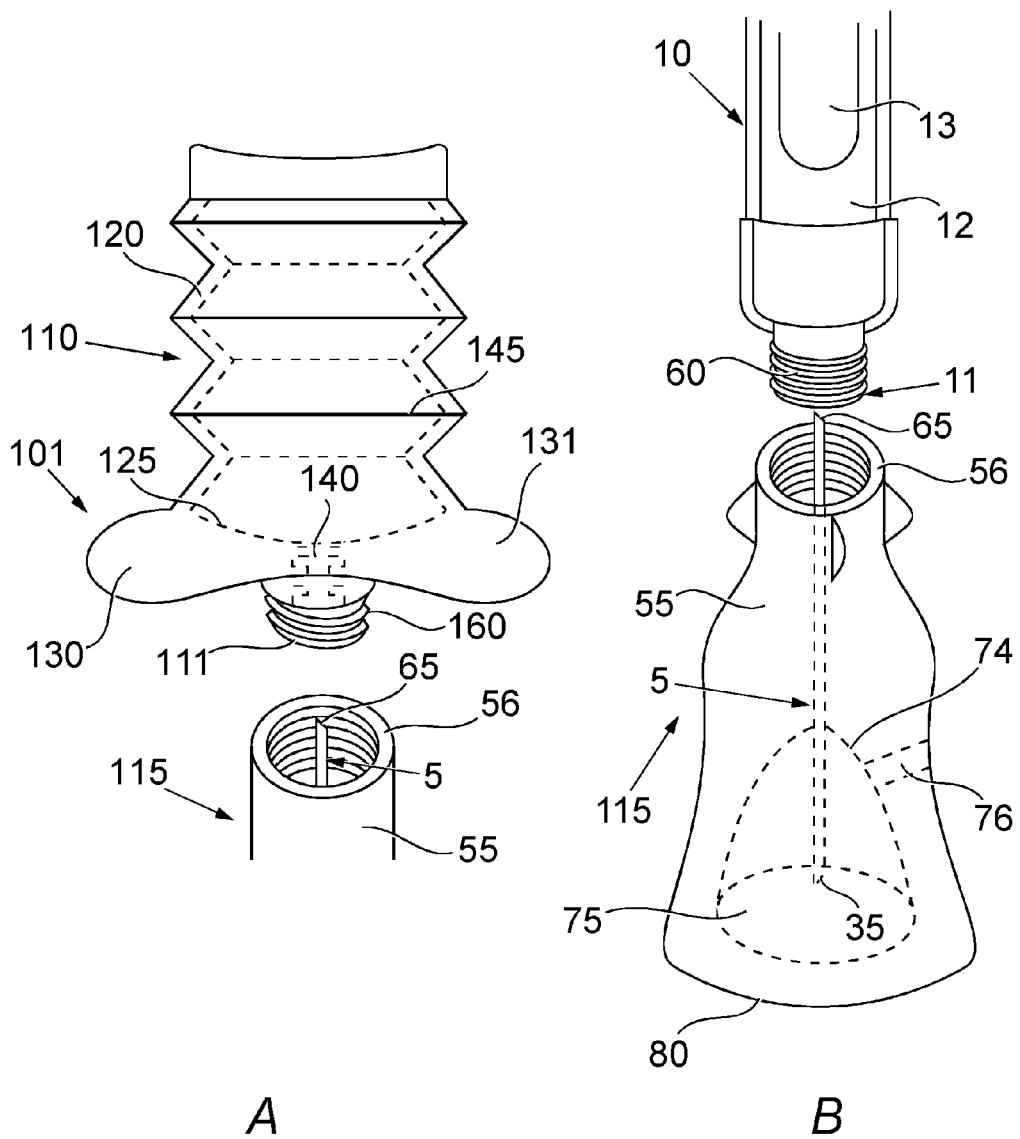
Figure 7:
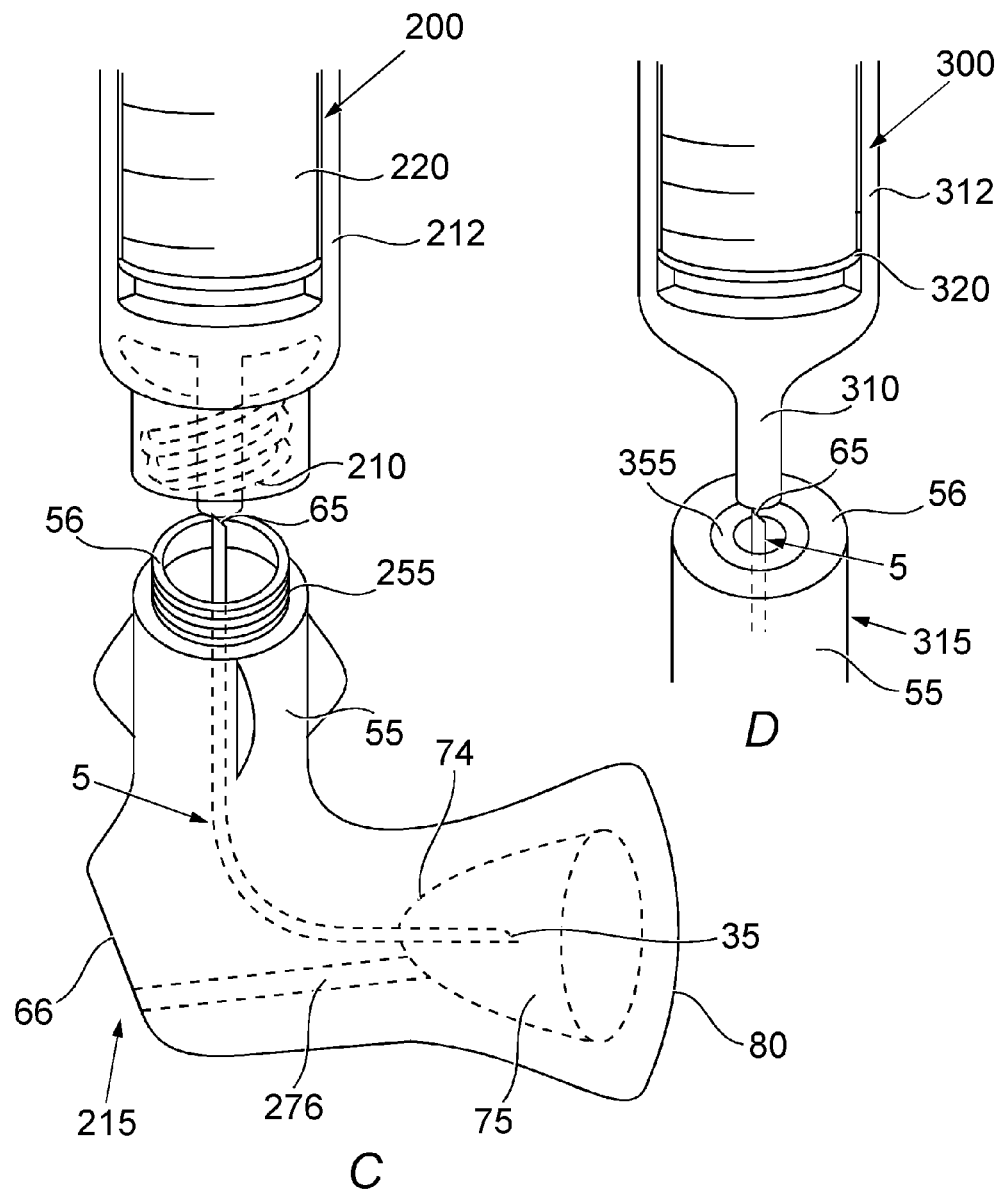

FIGS. 7A-D depict various types of needle housing and sources of injectable fluid in accordance with the invention. FIG. 7A shows an external view of the container 110 and needle housing 115 depicted in FIG. 6. The features of FIG. 6 in common with FIG. 7A are identically labelled in FIG. 7A. Only the distal end 56 of needle housing 115 is shown in FIG. 7A.

FIG. 7B shows the breech-loading syringe 10 of the embodiment of the invention depicted in FIG. 1 for connection with the needle housing 115 shown in FIGS. 5, 6 and 7A. The features of FIGS. 1, 5, 6 and 7A in common with FIG. 7B are identically labelled in FIG. 7B.

FIG. 7C shows a needle housing 215 for connection with a plastic syringe 200 with a male Luer lock fitting 210 at its proximal end. The plastic syringe 200 comprises a cylindrical tube 212 and a plunger 220 which is slidably fitted within the tube 212. The needle housing 215 is identical to needle housing 15 of FIGS. 1-4 except that collar 55 comprises annular rim 255 at its distal end 56 and that needle housing 215 is provided with a gas permeable section 276 connecting chamber 75 to depression 66. As is known in the art, annular rim 255 is shaped such that distal end 56 forms a female Luer lock fitting which is connectable to male Luer lock fitting 210 of plastic syringe 200. Connecting chamber 75 to depression 66 via a gas permeable section 276 means that the user can control with their finger (by covering the end of the section 276) the outflow of air when filling the chamber 75 with an injectable fluid. Gas permeable section 276 could be replaced with a vent.

FIG. 7D shows a needle housing 315 for connection with a plastic syringe 300 with a male Luer slip fitting 310 at its proximal end. The plastic syringe 300 comprises a cylindrical tube 312 and a plunger 320 which is slidably fitted within the tube 312. The needle housing 315 is identical to needle housing 15 of FIGS. 1-4 except that the internal cylindrical cavity at distal end 56 of collar 55 comprises a Luer taper 355 instead of a screw thread. As is known in the art, Luer taper 355 is shaped such that distal end 56 forms a female Luer slip fitting which is connectable to male Luer slip fitting 310 of plastic syringe 300.

The invention claimed is:

1. A needle housing having a distal end which is removably connectable to a source of injectable fluid and a proximal end for contacting a patient, the needle housing comprising:
    a) a hollow needle through which the injectable fluid is deliverable to the patient, the needle having a proximal end for insertion into body tissue of the patient; and
    b) a chamber having an open proximal end, the chamber surrounding at least part of the needle and extending proximally beyond the proximal end of the needle to the open proximal end, wherein the open proximal end of the chamber comprises a lip which is deformable and resiliently sealable against the body tissue of the patient, and wherein the open proximal end is moveable relative to the needle from a position in which the chamber extends proximally beyond the proximal end of the needle to a position in which the proximal end of the needle extends proximally through the open proximal end of the chamber,
    wherein the needle housing comprises a closable gas permeable section which connects the chamber to an exterior of the housing but is not permeable to the injectable fluid.

2. The needle housing as claimed in claim 1, wherein the chamber is collapsible and deformable.

3. The needle housing as claimed in claim 1, wherein the chamber and the open proximal end comprises a deformable plastic.

4. The needle housing as claimed in claim 3, wherein the chamber is collapsible and deformable to an extent that, in use, allows the needle to pierce the body tissue of a patient.

5. The needle housing as claimed in claim 1, wherein the proximal end of the needle is bevelled.

6. The needle housing as claimed in claim 1, comprising a substantially rigid connector at its distal end.

7. The needle housing as claimed in claim 1, wherein the needle housing is connectable to the source of injectable fluid by an interference fitting, a friction fitting, a Luer lock, or a screw thread.

8. The needle housing as claimed in claim 1, wherein the needle has a distal end which protrudes distally at the distal end of the housing.

9. The needle housing as claimed in claim 8, wherein the distal end of the needle is bevelled.

10. The needle housing as claimed in claim 1, wherein the needle is bent.

11. The needle housing as claimed in claim 10, wherein the needle is bent through an angle of at least 30 degrees.

12. The needle housing as claimed in claim 1, wherein the chamber is substantially bell-shaped.

13. The needle housing as claimed in claim 1, wherein the proximal end of the needle housing additionally comprises an end cap which is removably attachable to the open proximal end of the chamber.

14. The needle housing as claimed in claim 1, wherein the source of injectable fluid comprises a syringe.

15. The needle housing as claimed in claim 1, wherein the injectable fluid comprises a local anaesthetic.

16. The needle housing as claimed in claim 1, wherein the open proximal end of the chamber has an area of 3.5 square centimeters or less.

\* \* \* \* \*